(12) United States Patent
Megson

(10) Patent No.: US 9,131,677 B2
(45) Date of Patent: Sep. 15, 2015

(54) ORGAN PRESERVATION SOLUTION

(75) Inventor: Ian L. Megson, Inverness (GB)

(73) Assignee: University Court of the University of Edinburgh, Edinburgh Lothian (GB)

( * ) Notice: Subject to any disclaimer, the term of this patent is extended or adjusted under 35 U.S.C. 154(b) by 712 days.

(21) Appl. No.: 12/306,332

(22) PCT Filed: Jun. 28, 2007

(86) PCT No.: PCT/GB2007/002420
§ 371 (c)(1),
(2), (4) Date: May 6, 2009

(87) PCT Pub. No.: WO2008/001096
PCT Pub. Date: Jan. 3, 2008

(65) Prior Publication Data
US 2009/0305222 A1    Dec. 10, 2009

(30) Foreign Application Priority Data
Jun. 29, 2006    (GB) .................................. 0612877.1

(51) Int. Cl.
*A01N 1/00*    (2006.01)
*A01N 1/02*    (2006.01)

(52) U.S. Cl.
CPC ................ *A01N 1/02* (2013.01); *A01N 1/0221* (2013.01); *A01N 1/0226* (2013.01)

(58) Field of Classification Search
None
See application file for complete search history.

(56) References Cited

U.S. PATENT DOCUMENTS 4,879,283 A    11/1989 Belzer et al.

FOREIGN PATENT DOCUMENTS

| WO | WO 87/01940 | | 4/1987 |
| WO | WO 01/65935 | | 9/2001 |
| WO | WO 01/65935 A1 | * | 9/2001 |

OTHER PUBLICATIONS

Quintana et al (Annals of Hepatology, 2003, 2(2): 84-91).*
Gorren et al (Arch Biochem Biophys, 1996, 330(2): Abstract).*
Balazy et al (JBC, 1998, 273(48): 32009-23015).*
Gorren et al (Archives of Biochemistry and Biophysics, 1996, 330(2): 219-228).*
Tsikas et al (Journal of Chromatography, 2001, 107-116).*
Smith et al (Nitric Oxide, 2000, 4(1): 57-66).*
O'Donnell et al (Chem Res Toxicol, 1999, 12: 83-92).*
Konorev et al. "S-nitrosoglutathione improves functional recovery in the isolated rat heart after cardioplegic ischemic arrest-evidence for a cardioprotective effect of nitric oxide", *J. Pharmacology and Experimental Therapeutics* 274(1):200-6 (1995).
Salas et al. "S-nitrosoglutathione inhibits platelet activation and deposition in coronary artery saphenous vein grafts in vitro and in vito", *Heart (British Cardiac Soc.)* 80(2):146-50 (1998).
Yur-Ren et al. "Nitrosoglutathione improves blood perfusion and flap survival by suppressing iNOS but protecting eNOS expression in the flap vessels after ischemia/reperfusion injury", *Surgery* 135(4):437-46 (2004).
Gage et al. "Normalization of nitric oxide flux improves physiological parameters of porcine kidneys maintained on pulsatile perfusion", *Nitric Oxide: Biology and Chem./Official Journal of the Nitric Oxide Soc.* 9(3):141-7 (2003).
Quintana et al. "The benefit of adding sodium nitroprusside (NPNa) or S-nitrosoglutathion (GSNO) to the University of Wisconsin solution (UW) to prevent morphological alterations during cold preservation/reperfusion of rat livers", *Annals of Hepatology: Official Journal of the Mexican Association of Hepatology* 2(2):84-91 (2003).
Notification of the Transmittal of the International Search Report and the Written Opinion of the International Searching Authority, or the Declaration corresponding to International Application No. PCT/GB2007/002420 mailed Oct. 28, 2008.
Written Opinion of the International Searching Authority corresponding to International Application No. PCT/GB2007/002420 mailed Oct. 28, 2008.

* cited by examiner

*Primary Examiner* — Sean Aeder
(74) *Attorney, Agent, or Firm* — Myers Bigel Sibley & Sajovec, PA

(57) ABSTRACT

The invention relates to the field of organ and biological tissue preservation and in particular to solutions for use in preserving organs and/or tissues prior to transplanting into a subject.

5 Claims, 5 Drawing Sheets

(a)

1h

(b)

48 h

ORGAN PRESERVATION SOLUTION

CROSS-REFERENCE TO RELATED APPLICATIONS

This application is a 35 U.S.C. §371 national phase application of PCT Application No. PCT/GB2007/002420, filed on Jun. 28, 2007, which claims priority from Great Britain Patent Application No. 0612877.1, filed on Jun. 29, 2006, the disclosures and contents of which are incorporated by reference herein in their entireties. The above-referenced PCT International Application was published in the English language as International Publication No. WO 2008/001096.

FIELD OF THE INVENTION

The invention relates to the field of organ and biological tissue preservation and in particular to solutions for use in preserving organs and/or tissues prior to transplanting into a subject.

BACKGROUND OF THE INVENTION

Organ preservation aims to maintain the donor organ in an optimal morphological and biochemical state from the time of retrieval to the time of transplantation. Cold organ storage must withstand the insults of initial cold ischaemia and subsequent reperfusion injury on implantation.

Although this method of organ preservation is effective and has increased the safe time for organ preservation, some organs do not function well upon transplant and exhibit primary organ dysfunction[1]. Primary organ dysfunction is associated with the duration of cold ischaemia and, possibly, with reperfusion-related injury[2]. Thus, despite the ongoing progress on short- and long-term graft survival, primary organ dysfunction remains a problem and target for therapeutic intervention.

Endothelial dysfunction is an important mediator in the development of ischaemia-reperfusion injury (IRI) and graft rejection[3,4]. Protection of the vascular endothelium is a critical factor in organ preservation. This monolayer of cells that lines all healthy blood vessels normally releases endothelium-derived relaxing factors to help maintain blood flow in the microcirculation, to help prevent adhesion or inflammatory cells and platelets that predispose to inflammation and thrombosis[5].

University of Wisconsin (UW) solution has revolutionised cold ischaemic preservation of solid organs, permitting safe preservation times of up to 72 hours. It now remains the most widely utilised solution for cold preservation of intrabdominal organs. The composition of UW solution was designed to counter the theoretical problems associated with cold ischaemic preservation, namely to minimise hypothermic-induced cell swelling, prevent intracellular acidosis, prevent expansion of interstitial space and prevent oxygen free radical induced injury[6].

There has been little change to the components of UW solution since its conception but, in vitro and in vivo studies have shown that many of the components of UW solution confer little benefit. These studies have suggested that it is possible to improve upon UW solution by simplification and the elimination of several components; only lactobionate, raffinose and glutathione have been considered as truly essential[7]. However, clinical trials in renal transplantation have shown that glutathione supplementation to UW solution confers no clinical advantage[8].

Glutathione (GSH) is added to UW organ preservation solution and other preservation solutions, such as Celsior and Belzer MPS solutions on the premise that it protects against oxidative stress during cold ischemia. However, one disadvantage is that the glutathione is often required to be added immediately prior to use as the preservation solution, as it oxidises during storage.

There has been a suggestion that the provision/production of low amounts of nitric oxide to the organ/tissue may be beneficial. Vodovotz (Nitric Oxide 2003 November; 9(3): 141-7) for example showed that the combination of suppression of harmful amounts of NO, while supplying a constant low-level amount of NO, may improve pulsatile kidney preservation using Belzer MPS comprising gluthatione. Quintana et al (Int. J. Surg. Investig. 2001; 2(5): 401-411) also looked at the addition of S-nitrosoglutathione (GSNO) to UW solution and observed that GSNO as a NO donor can improve UW solution properties to preserve rat liver by maintaining the hepatic morphology and avoiding hepatic injury post cold preservation/reperfusion.

It is amongst the objects of the present invention to obviate and/or mitigate at least one of the aforementioned disadvantages.

It is a further object of the invention to provide an organ preservation solution with at least one advantage over the existing UW and/or related solutions.

The present invention is based on studies by the inventors to assess the impact of glutathione (GSH) supplementation of UW solution on endothelial function in a model of cold ischaemia-reperfusion and to establish whether the cell permeant monoethyl ester of GSH (GSH-MEE) or the GSH-related nitric oxide (NO) donor, S-nitrosoglutathione (GSN), might have any beneficial effect on vascular function and endothelial cell survival, in the face of oxidative stress.

In a first aspect there is provided a solution for use in organ and/or tissue preservation, wherein the solution comprises a source of a S-nitrosothiol, with the proviso that the solution is substantially free of glutathione or glutathione forming compounds, when in use as a preservation solution.

As mentioned in the background to the invention, glutathione and/or glutathione forming compounds are often added or included in organ reperfusion solutions such as UW. The present invention is based in part on the use of solutions which are free or substantially free of glutathione or glutathione forming compounds. By substantially free is understood to mean less than 50 µM levels, glutathione conventionally being used in mM amounts. Glutathione forming compounds include N-acetylcysteine, cysteine or glutathione disulphide. It should be noted that prior art organ preservation solutions can be stored free of glutathione prior to use, but that glutathione, or glutathione forming compounds may be added prior to, or just before use. The present invention therefore relates to an organ preservation solution formulated as it is intended to be administered to a subject.

Typically the S-nitrosothiol is S-nitroglutathione. The S-nitrosothiol, such as S-nitrosoglutathione may typically be added in an amount of 1 µM-1 mM, such as 20 µM-500 µM.

The organ preservation solution of the present invention will naturally comprise other components known and used in other preservation solutions such as UW (see U.S. Pat. Nos. 4,798,824 and 4,879,283, for example), Celsior and Belzer MPS solutions. Other components may include acid-base buffers to help maintain the pH of the solution. Typical buffers may be based on phosphates, such as $KH_2PO_4$. There are also likely to be sources of potassium and sodium and the solution may have to have a desired osmolarity.

Other components may include, or be selected from starch; hydroxyethyl starch; lactobionic acid; sodium and/or potassium gluconate; glucose; $CaCl_2$; potassium phosphate; EDTA or other metal chelating agent such as chelex magnesium sulphate; raffinose; dextran; recombinant albumin; protective agents against ischaemic insult, such as adenosine; antioxidants, such as allopurinol and/or pentafraction, with the components being made up in water. Additional optional components may include antibiotics, such as penicillin; insulin (to aid in glucose uptake) and/or anti-inflammatories such as dexanethasone.

The use of EDTA or other metal chelating agent may be particularly advantageous, as transition metal ions may have an undesirable effect on S-nitrosoglutathione and their removal/chelation would be desirable.

It may also be desirable to protect the solution from light, during storage. Thus, the solution may be stored in an opaque or semi-opaque container prior to use.

Thus in a further aspect, the present invention provides a substantially light impermeable package wherein the package contains within a solution according to the present invention. By light impermeable is understood to mean ambient light as found in conventional environment where such packages would be stored/transported.

It may be desirable during storage, prior to use of the solution, for the GSNO to be kept separate from the other components, in order to help maintain shelf-life of the solution. In this manner, the GSNO may be added or admixed with the other components shortly before or immediately before use to preserve organs and/or tissues (e.g. several hours to minutes before use, e.g. 6-2 hours to 10 mins, 5 mins, etc.).

The GSNO may be added as a solid to a solution comprising the other components, or may itself be in solution, such as dissolved in a suitable stabilising solvent, such as DSMO, optionally dissolved in water in a 1:1-4:1 ratio: DMSO/DMF: water or DMF.

For ease of use, the solution comprising all necessary components, other than GSNO may be provided in a container such as a bag etc. to which the GSNO may be added. The GSNO may be found in a rupturable compartment adjacent or within the container, such that prior to rupturing of a membrane, wall or the like the rupturable compartment, the FSNO is kept separate from the other components, but upon rupturing, the GSNO is able to mix with the other components and become part of the solution.

Thus, for example, GSNO may be stored in DMSO (e.g. 50-100% in deionised or distilled water; <5 ml) in for example a pocket, bubble or syringe device that forms an integral part of a bag or packaging that contains the preservation solution. The GSNO will preferably be protected from light whilst in the storage vessel. Under refrigerated conditions, the GSNO in DMSO will form a frozen mass, which is separated from the organ preservation solution by a impermeable membrane or foil. Immediately prior to use, the GSNO-containing DMSO solid will be pushed through the membrane or foil, whereupon it will dissolve rapidly in the aqueous solution to give a final concentration of GNSO within the desired range (1 μM-1 mM) and a final DMSO concentration generally not exceeding 1% of the final organ preservation solution.

A particularly preferred formulation is as follows:

| | |
|---|---|
| S-nitrosoglutathione | 50 μM-200 μM |
| Lactobionate | 50 mM-200 mM |
| $KH_2PO_4$ | 10 mM-100 mM |

-continued

| | |
|---|---|
| $MgSO_4$ | 1 mM-20 mM |
| Carbohydrate source (e.g. raffinose, glucose or sucrose) | 2 mM-50 mM |
| Metal chelator (e.g. EDTA, or chelex) | 0.01 mM-1 mM |
| protective agent against ischaemic insults, such as adenosine | 1 mM-10 mM |
| antioxidant, such as allopurinol | 100 μM-5 mM |
| anti-inflammatory, such as dexamethasone | 5 mg/l-30 mg/l |
| insulin | 10 u/l-100 u/l |
| antibiotic(s), such as penicillin | 50 mg/l-250 mg/l |

Alternatively, a preferred solution is simply the UW solution without glutathione, but including S-nitrosoglutathione at a concentration of 50 μM-200 μM.

A preservation solution of the present invention may be prepared by mixing the desired components with an amount of water, such as distilled and/or deionised water and then making up to the appropriate quantity using further water. For example, if the quantity is say 10l, then the components may first be dissolved in 7-9l and once the compounds have dissolved (the pH may then be adjusted to, for example pH 7.3, by the addition of acid and/or base), and further water can be added in order to make the solution up to 10l. As the solutions of the present invention do not include glutathione, it is expected that they will have a relatively long shelf-life of typically over 1 month when refrigerated and the GSNO is not stored as part of the solution. The present inventor has observed that GSNO decomposes over time when kept refrigerated within a typical organ preservation solution. However, when GSNO is stored within a preserving solvent, such as a solution of DMSO, stability of the GSNO can be maintained over long periods—see Examples Section.

It is to be understood that the preservation solutions of the present invention may be used simply to store the organ or tissue requiring to be preserved, and/or the solution may be perfused through the tissue, using procedures and/or machines known in the art. Typically preservation may be conducted at reduced temperature, such as 2-10° C. and prior to use the organ and/or tissue may be reperfused with a solution at or close to body temperature, such as about 37° C.

Typical organs and/or tissues which may be preserved using the solutions of the present invention include kidney, liver, heart, lung, pancreas and the like and the organ/tissue may be obtained, although not necessarily so, from a cadaver. It may also include vessels such as veins or arteries which may be grafted to a patient. Typically the subject is a human subject, but other animals may also receive transplants and as such the solution may be used to preserve non-human animal organs/tissue.

In a further aspect there is provided a method of preserving an organ and/or tissue, comprising the steps of:
 a) obtaining the organ and/or tissue from a suitable source; and
 b) maintaining the organ and/or tissue in a solution of the present invention and/or reperfusing a solution of the present invention through the organ and/or tissue.

Solutions based on, or similar in composition, are expected to be able to preserve/used to store organs for at least 24-48 hrs, as this is how long UW solutions can be used, but have the advantage of not having glutathione present and including S-nitroso glutathione.

There is also provided use of a S-nitrosothiol, especially S-nitroglutathione for the preparation of an organ preservation solution wherein the organ preservation solution is free or substantially free of glutathione or glutathione forming compounds, when formulated for use.

The present invention will now be further described by way of example and with reference to the Figures which show:

Figure 5:
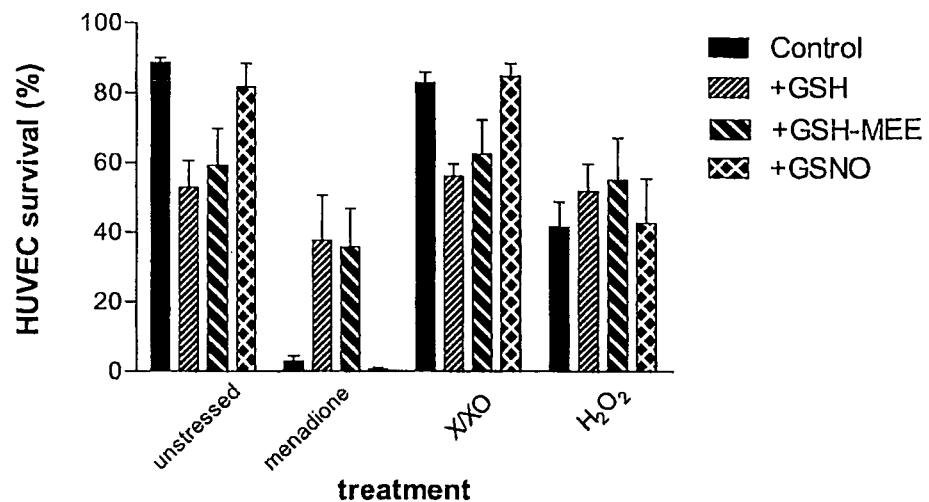
Figure 6:
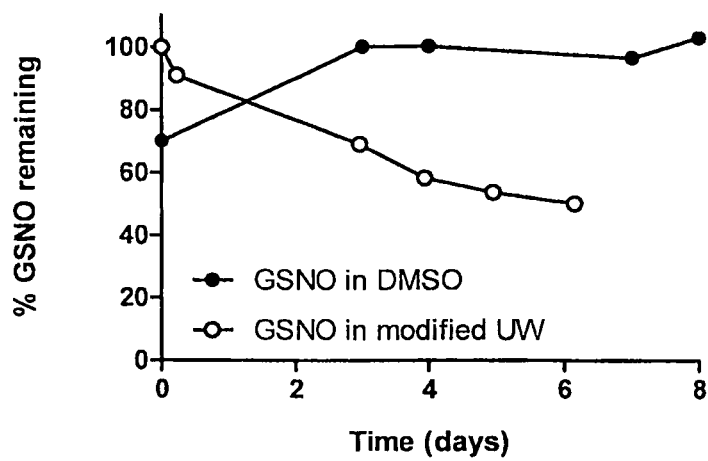

FIG. 5 shows comparison of human umbilical vein endothelial cell (HUVEC) survival after 24 h incubation under standard (unstressed) conditions or in the presence of the hydroxyl radical generator, menadione (10 μM), the superoxide generating system, xanthine/xanthine oxidase (X/XO; 5 μM, 1 mU/ml) or $H_2O_2$; 100 μM). *P<0.05; P<0.01; *P<0.001; ns—not significant; and FIG. 6 shows decomposition of relevant concentrations of GSNO in modified UW solution (100 Mm GSNO) and DMSO (1 mM GSNO) over 6-8 days at 4-6° C. in the dark (refrigerator), as assessed by monitoring the absorbance at 339 nm (characteristic of the S—NO bond).

Materials and Methods

Animal care and experimental protocols were performed in accordance with the Home Office Guidance in the Operation of Animals (Scientific Procedures) Act 1986, UK. Adult male Wistar rats weighing 300-450 g were kept in a temperature-controlled environment with a 12 h light-dark cycle, and allowed free access to water and standard diet. University of Wisconsin solution was prepared according to standard protocol: Potassium lactobionate 100 mM, $KH_2PO_4$ 25 mM, $MgSO_4$ 5 mM, raffinose 30 mM, adenosine 5 mM, allopurinol 1 mM, dexamethasone 16 mg/L, insulin 40 U/L, penicillin 200 000 U/L and EDTA 0.03 mM at pH 7.4. The EDTA was added in order to help protect GSNO against metal-ion catalysed decomposition. The solution was bubbled with argon gas for 1 hour to mimic hypoxia. Oxygen levels were confirmed using an oxygen electrode (Apollo 4000 integrated free radical analyser, World Precision Instruments Inc. USA). Bubbling for 30 minutes depleted >90% of oxygen in solution.

Experimental Protocol

Following cervical dislocation, laparotomy was performed and the aorta dissected with clearance of periaortic fat and connective tissue. Vessels were divided into 3-5 mm aortic rings with care taken not to stretch or damage the vessels. Aortic rings were subjected to cold ischaemic storage (4° C. for 1 or 48 hours) in sealed containers filled with hypoxic control (UW without GSH) solution; UW with GSH (3 mM); UW with glutathione monoethyl ester (GSHMEE; 3 mM) or UW with S-nitrosated glutathione (GSNO; 100 μM).

After storage, aortic rings were suspended between two stainless steel supports in a myograph (700MO, Danish Myo, Aarhus, Denmark) and reoxygenated in 10 ml organ baths containing Krebs buffer solution (mM): NaCl 118, KCl 4.7, $NaHCO_3$ 25, $KH_2PO_4$ 1.17, $MgSO_4.7H_2O$ 1.2, Glucose 5.5, EDTA 0.03 and $CaCl_2.2H_2O$ 1.6 (37° C.; pH 7.4). Changes in isometric tension were detected by a transducer and recorded using a MacLab data acquisition system (MacLab 8 with Chart v 3.5; AD Instrument, Hastings, UK) and displayed on a Macintosh Performa 630 computer. Resting tensions of 1.5 g were applied to all rings prior to equilibration (30 minutes).

Following equilibration, all vessels were exposed to Krebs buffer containing a high concentration of potassium (60 mM) three times to assess tissue viability and to provide a reference maximum contraction for subsequent data analysis. Each response was followed by a washout. A concentration-response curve to the $\alpha_1$ adrenoceptor agonist, L-phenylephrine (PE; $10^{-8}M-3\times10^{-5}M$) was then constructed and used to identify the concentration of PE required to generate ~80% maximal contraction ($EC_{80}$) for subsequent vasodilator studies. Upon establishing stable contractions, cumulative concentration-response curves to the endothelium-dependent vasodilator, acetylcholine (ACh; $10^{-9}-10^{-5}M$) were constructed in all preparations. Only one concentration-response curve was obtained per tissue. A further submaximal PE contraction was elicited and the NO synthase inhibitor, $N^{\omega}$-nitro-L-arginine methyl ester (L-NAME) was applied to inhibit endogenous NO production and to determine the vasodilatory effect of endothelium-derived NO under basal (unstimulated) conditions. Subsequently, the NO scavenger, carboxy-PTIO (cPTIO; 1 mM), was added in order to establish the contribution of NOS-independent NO to any vasodilator tone existing under basal conditions.

Endothelial Cell Viability Assay

Human umbilical vein endothelial cells (HUVEC) were seeded in 162 ml flasks (Dulbecco's modified Eagle's medium 37° C., 5% $CO_2$). Cells were cultured to confluence and transferred to 6-well culture dishes containing phosphate buffered saline (control), UW without GSH, UW+GSH (3 mM), UW+GSH-MEE (3 mM) or UW+GSNO for 24 h (37° C.) in the absence of any oxidants or in the presence of a hydroxyl radical generator (menadione; 10 μM), the superoxide generating system, xanthine+xanthine oxidase (5 μM; 1 mU/ml) or the oxidant species $H_2O_2$ (100 μM). Cell viability after 24 h incubations was assessed using a standard trypan blue exclusion assay.

Statistical Analysis

Statistical analysis was performed using GraphPad Prism version 3.02 for Windows, GraphPad Software, San Diego Calif. USA. All values are expressed as means+/−SEM. Data were analysed by one-way or two-way ANOVA; Dunnet's post-hoc test was applied where appropriate following one-way ANOVAs. P<0.05 was considered significant.

Results

Figure 1:
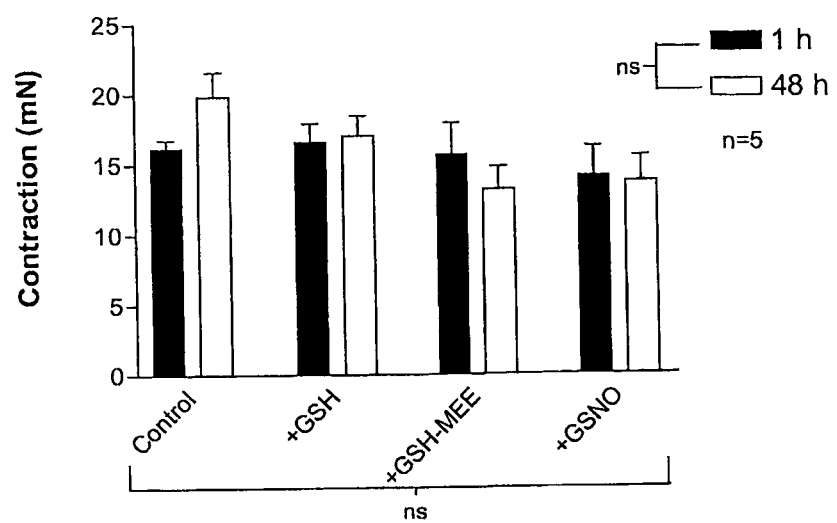
FIG. 1 shows maximum contraction of aortic rings subjected to 1 h or 48 h of cold ischaemia in UW solutions to KCl (60 mM)

Potassium chloride (60 mM) generated reproducible contractions of the aortic rings after 1 h or 48 h of cold ischaemia in UW solution with and without GSH analogue supplementation. There was no significant difference in the magnitude of contraction elicited in rings stored in any solution (P=0.061; FIG. 1).

Figure 2:
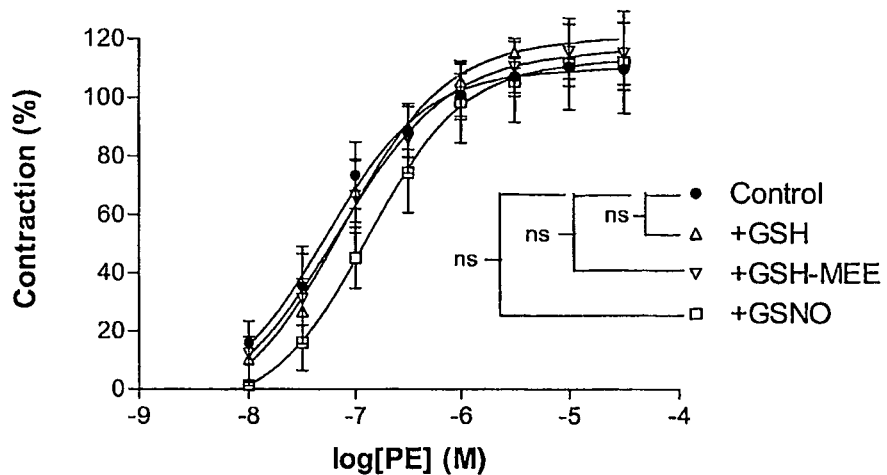
FIG. 2 shows concentration dependent curves of aortic rings subjected to phenylephrine (PE) after a) 1 h cold storage in UW solutions. b) 48 h cold storage in UW solutions. ***P<0.001, ns—not significant.
Figure 2:
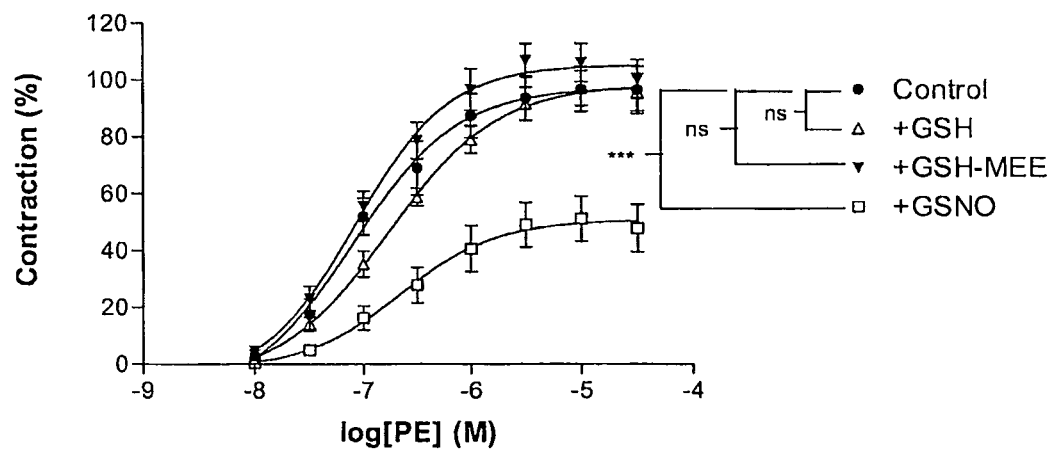

Phenylephrine (10-100 nM) caused a stable contraction of each preparation equivalent to ~80% of the maximal response to 60 mM KCl. After 1 h cold ischaemia, there was no significant difference in maximal PE-induced contraction between any of the UW solutions and standard UW (FIG. 2a). After 48 h cold ischaemia, tissue stored in GSNO supplemented UW was the only one to exhibit significantly depressed maximal contractions to PE than GSH-free UW (FIG. 2b).

Figure 3:
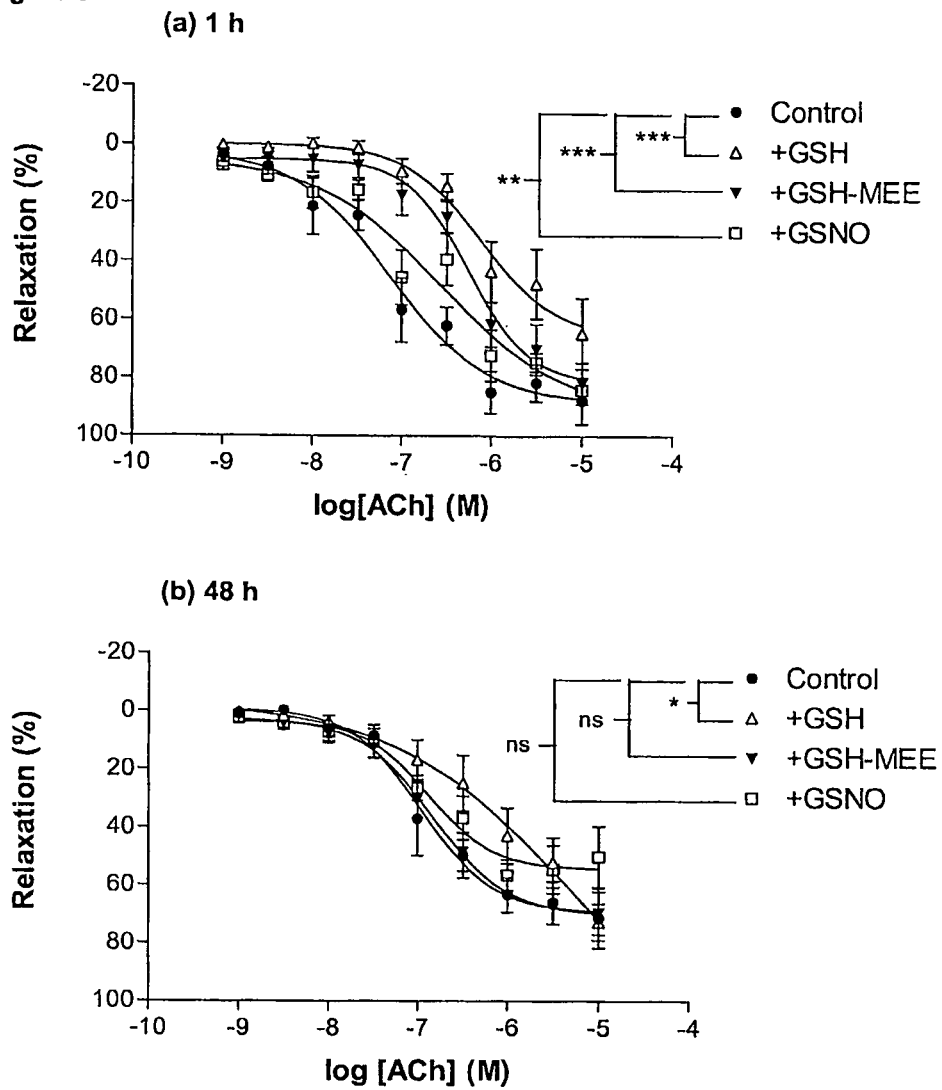
FIG. 3 shows concentration dependent curves of aortic rings subjected to acetylcholine (ACh) after a) 1 h or b) 48 h cold storage in UW solutions. *P<0.05, P<0.01, *P<0.001, ns—not significant.

Acetylcholine (10-100 nM) elicited concentration-dependent vasorelaxation in PE precontracted aortic rings after 1 h or 48 h of cold ischaemia in all UW solutions. After 1 h cold ischaemia, tissues stored in GSH-free UW displayed significantly greater endothelium-dependent relaxation than any of the tissues stored in GSH analogue supplemented solutions (FIG. 3a). After 48 h cold ischaemia, all vessels showed depressed responses to Ach compared to their 1 h counterparts, but tissues stored in UW supplemented with GSH displayed significantly poorer endothelium-dependent relaxation than GSH-free UW. There was no significant difference in endothelium dependent relaxation between tissues stored in either GSNO or GSHMEE supplemented UW and GSH-free UW (FIG. 3b).

Figure 4:
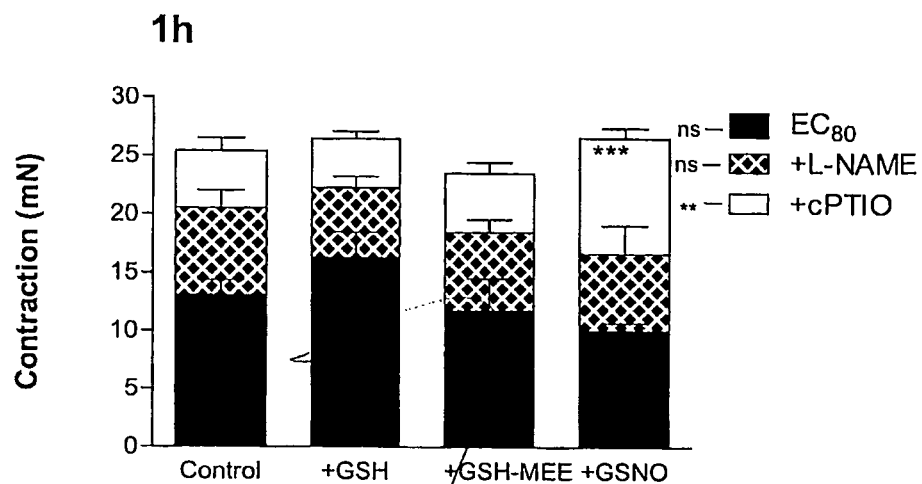
FIG. 4 shows contractile response of aortic rings to PE ($EC_{80}$)) and the effect of subsequent treatment with the NO synthase inhibitor, L-NAME (100 mM) and the NO scavenger, cPTIO after a) 1 h or b) 48 h cold storage in UW solutions. *P<0.05; P<0.01; *P<0.001; ns—not significant.
Figure 4:
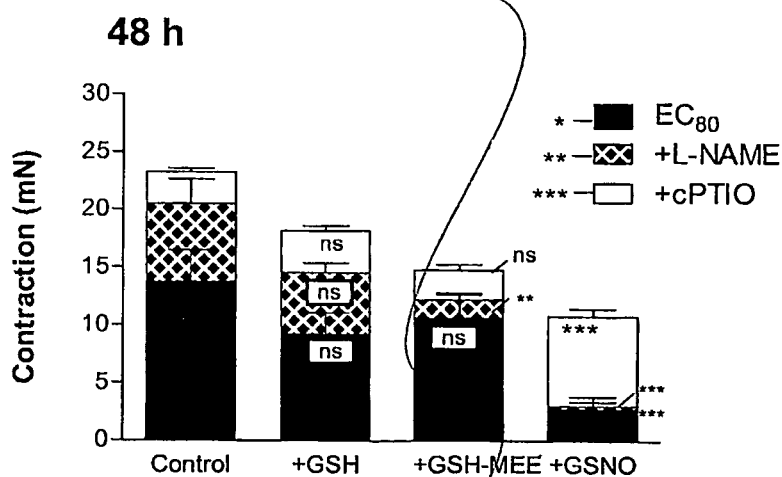

The addition of L-NAME to precontracted tissues after 1 h cold ischaemia in any GSH analogue supplemented UW solution caused a similar contraction compared to that in vessels treated with GSH-free UW (FIG. 4a). The further addition of the NO scavenger, cPTIO, caused a significantly greater contraction only in tissues stored in GSNO supplemented UW compared to standard UW (FIG. 4a).

The addition of L-NAME to precontracted tissues after 48 h cold ischaemia in either GSHMEE or GSNO supplemented UW solution caused a significantly lesser contraction compared to standard UW (FIG. 4b). Once again, the further addition of cPTIO caused a significantly greater contraction only in tissues stored in GSNO supplemented UW compared to standard UW (FIG. 4b).

Cell Viability Assay

HUVEC cell viability after 24 h in control phosphate buffered saline medium was >80% (FIG. 5). Cells incubated in GSH- or GSH-MEE-containing UW had a significantly reduced viability, whilst those in UW+GSNO had a survival rate not significantly different from control. The hydroxyl radical generator was highly cytotoxic, with less than 5% of cells surviving the 24 hr treatment period under control conditions. GSH and GSH-MEE significantly enhanced cell survival in the presence of menadione whilst GSNO was ineffective. The superoxide generating system, X/XO, failed to significantly affect cell survival and the pattern of responsiveness to the various treatments was the same as that found under unstressed conditions. $H_2O_2$ caused substantial cell death, but none of the UW treatments had a significant effect on cell viability.

Discussion

Cold ischaemia and ischaemia-reperfusion injury are characterised by oxidative stress, to which endothelial cells are particularly sensitive, not only in terms of cell viability, but also through inactivation of the powerful endothelium-derived protective agent, nitric oxide (NO) by oxygen-centred free radicals. The resulting vasoconstriction, together with increased tendency for platelet aggregation, monocyte adhesion and leukocyte activation are critical limitations to organ preservation[5].

Glutathione (GSH) is a key element in intracellular antioxidant defenses, where it can act as an antioxidant in its own right, as a provider of reducing equivalents for antioxidant enzymes and as an endogenous reducing agent for recycling vitamins C and E[9,10]. Importantly, GSH is vital to the protection of endothelial cells from oxidative damage[11]. Delivery of GSH is, therefore, a theoretically beneficial means of increasing the antioxidant capacity of cells and of protecting the integrity and function of endothelial cells in particular. On this basis, it seems logical to fortify organ preservation solutions like UW with GSH, in an effort to help protect against oxidative damage.

Previous in vitro and in vivo work has suggested that the addition of GSH to organ preservation solution confers no advantage[8]. This lack of benefit is likely to be due to the fact that GSH in UW is rapidly oxidised to its inactive form during storage prior to use; the half life of GSH in UW solution is recognised to be around 8 days under cold storage. Furthermore, GSH is a tripeptide and does not readily cross cell membranes[12]. Given that intracellular free radicals will not cross membranes either, this presents a problem for successful replenishment of depleted intracellular stores under conditions of oxidative stress. Glutathione in UW is likely, therefore, to act primarily as a short-lived extracellular antioxidant during the ischaemic period, and to have only limited benefit upon organ reperfusion after transplantation.

After 1 h or 48 h cold ischaemia in any of the UW solutions, smooth muscle function appears to be preserved as demonstrated by the PE concentration dependent curves. The finding that rings stored in GSNO-supplemented UW for 48 h have a lesser contractile response may be a reflection of exogenous NO activity causing a vasorelaxant effect, despite the fact that GSNO is washed out several hours before responses to phenylephrine are assessed. These findings are in keeping with our previous data showing that GSNO was able to sustain NO-mediated dilatation of segments of human saphenous vein and internal mammary artery for several hours after washout[13].

The present data show that after cold ischaemic storage for 1 h, endothelium-dependent vasodilatation is significantly impaired in tissues stored in UW solution supplemented by GSH analogues compared to tissues stored in standard UW solution. After 48 h cold ischaemia, only tissues stored in GSH supplemented UW exhibited this impairment of endothelial function. These data imply that GSH supplementation of UW solution has a detrimental effect on endothelial dysfunction during cold ischaemia that is rapid in onset and additional to that caused by ischaemia-reperfusion alone. The precise mechanism underlying this paradoxical effect is unclear, but it might be mediated by an exacerbation of free-radical-induced damage under these conditions. This hypothesis is supported by existing evidence for glutathionyl radical-induced peroxidation of phospholipids, resulting in cellular damage and by our endothelial cell culture experiments, whereby both GSH and GSH-MEE significantly reduced cell viability during a 24 hr exposure in the absence of an oxidant challenge[14]. GSNO did not induce cell death under these conditions, suggesting that this agent might be preferable not only on account of its NO-generating properties but also on its lack of cytotoxic effects at pharmacologically relevant concentrations. Furthermore, there is existing data to show that the delivery of exogenous NO is cytoprotective in ischaemia-reperfusion injury[15].

In conclusion, the current data do not support the addition of GSH to UW organ preservation solution; rather than conferring beneficial anti-oxidant properties, it may evoke a paradoxical cytotoxic effect. Whilst the cell-permeant adduct of GSH, GSH-MEE, appeared to have a less detrimental impact on endothelial function, it too was apparently toxic to endothelial cells. GSNO, on the other hand, did not share the cytotoxic properties of GSH and GSH-MEE, whilst also generating NO for several hours after washout to cause sustained vasodilatation that could help sustain perfusion in the early period following transplantation.

Our data indicate that GSNO in modified UW (containing EDTA but excluding GSH) decomposed with a half-life of ~6 days, when stored in a conventional laboratory refrigerator in the dark at 4-6° C. Over the same time period and in the same conditions, GSNO did not show any significant decomposition in 100% DMSO. The freezing point for DMSO is ~15° C., so these samples were effectively "frozen" for the duration of the experiment, perhaps contributing to the stability of GSNO under these conditions. The apparent depression of absorbance at time zero in the DMSO sample is most likely attributable to incomplete dissolution of the material when the first measurement was taken. The lack of significant GSNO decomposition in DMSO during this time period precluded determination of a meaningful half life, but it is likely to be of the order of several months.

REFERENCES

1. Southard J H, Belzer F O. Organ preservation. *Annual Review of Medicine*. 1995; 46:235-247.
2. Erkasap S, Ates E. L-Arginine-enriched preservation solution decreases ischaemia/reperfusion injury in canine kidneys after long term cold storage. *Nephrology Dialysis Transplant* 2000; 15: 1224-7
3. Hidalgo M A, Shah K A, Fuller B J, Green C J. Cold ischemia-induced damage to vascular endiothelium results in permeability alterations in transplanted lungs. *Journal of Thoracic & Cardiovascular Surgery.* 1996; 112: 1027-1035.
4. Rubanyi G M, Vanhoutte P M. Superoxide anions and hyperoxia inactivate endothelium-derived relaxing factor. *American Journal of Physiology.* 1986; 250: H822-H827.
5. Smedsrod B, De Bleser P J, Braet F, Lovisetti P, Vanderkerken K. Cell biology of liver endothelial and Kupffer cells. *Gut.* 1994; 35: 1509-1516
6. Belzer F O, Southard J H. Principles of solid-organ preservation by cold storage. *Transplantation* 1988; 45: 673-676.
7. Jamieson N V, Lindell S, Sundberg R, Southard J H, Belzer F O. An analysis of the components in UW solution using the isolated perfused rabbit liver. *Transplantation.* 1988; 46: 512-516.
8. Polyak M M, Arrington B O, Kapur S, Stubenbord W T, Kinkhabwala M. Glutathione supplementation during cold ischemia does not confer early functional advantage in renal transplantation. *Transplantation* 2000; 70: 202-205.
9. Flohe L, Gunzler W A. Glutathione-dependent enzymatic oxidoreduction reactions. In: Arias I M, Jakoby W B, eds. *Glutathione: metabolism and function*. New York: Raven Press; 1976:17-34
10. Kosower E M. Chemical properties of glutathione. In: Arias I M, Jakoby W B, eds. *Glutathione: metabolism and function*. New York: Raven Press; 1976:1-16.
11. Kugiyama K, Ohgushi M, Motoyama T, Hirashima O, Soejima H, Misumi K, et al. Intracoronary infusion of reduced glutathione improves endothelial vasomotor response to acetycholine in human coronary circulation. *Circulation.* 1998; 97: 2299-2301.
12. Boudjema K, van Gulik T, Lindell S, Vreugdenhill P, Southard J, Belzer F. Effect of oxidised and reduced glutathione in liver preservation. *Transplantation.* 1990; 50: 948-951.
13. Sogo N, Campanella C, Webb D J, Megson I L. S-nitrosothiols cause prolonged, nitric oxide-mediated relaxation in human saphenous vein and internal mammary artery: therapeutic potential in bypass surgery. *Br J Pharmacol.* 2000; 131: 1236-1244.
14. Borisenko G G, Martin I, Zhao Q, Amoscato A A, Tyurina Y Y, Kagan V E. Glutathione propagates oxidative stress triggered by myeloperoxidase in HL-60 cells. Evidence for glutathionyl radical-induced peroxidation of phospholipids and cytotoxicity. *J Biol Chem.* 2004; 279: 23453-23462.
15. Duranski M R, Greer J J, Dejam A, Jaganmohan S, Hogg N, Langston W, et al. Cytoprotective effects of nitrite during in vivo ischemia-reperfusion of the heart and liver. *J Clin Invest.* 2005; 115: 1232-40.

The invention claimed is:

1. An organ and/or tissue preservation solution, wherein the solution comprises a source of a S-nitrosothiol and a metal chelating agent, with the proviso that the solution comprises less than 50 µM glutathione or glutathione forming compounds when in use as a preservation solution, further comprising lactobionic acid, a carbohydrate source, a protective agent against ischaemic insults, an antioxidant, an anti-inflammatory, an aid to glucose uptake, and an antibiotic, wherein the S-nitrosothiol is S-nitrosoglutathione and the metal chelating agent is EDTA or chelex magnesium sulfate.

2. The organ and/or tissue preservation solution according to claim 1, wherein the carbohydrate source is raffinose, the protective agent against ischaemic insults is adenosine, the antioxidant is allopurinol, the anti-inflammatory is allopurinol, the aid to glucose uptake is insulin, the antibiotic is penicillin and the metal chelating agent is EDTA.

3. A method of preserving an organ and/or tissue, comprising the steps of:
   a) obtaining the organ and/or tissue from a suitable source; and
   b) maintaining the organ and/or tissue in a solution comprising a source of a S-nitrosothiol and a metal chelating agent, with the proviso that the solution comprises less than 50 µM glutathione or glutathione forming compounds when in use as a tissue preservation solution.

4. A method of preserving an organ and/or tissue, comprising the steps of:
   a) obtaining the organ and/or tissue from a suitable source; and
   b) reperfusing a solution comprising a source of a S-nitrosothiol and a metal chelating agent, with the proviso that the solution comprises less than 50 µM glutathione or glutathione forming compounds when in use as a tissue preservation solution, through the organ and/or tissue.

5. The method of claim 3, further comprising a step of:
   c) reperfusing through the organ and/or tissue a solution comprising a source of a S-nitrosothiol and a metal chelating agent, with the proviso that the solution comprises less than 50 µM glutathione or glutathione forming compounds when in use as a tissue preservation solution.

* * * * *

UNITED STATES PATENT AND TRADEMARK OFFICE
CERTIFICATE OF CORRECTION

PATENT NO. : 9,131,677 B2  
APPLICATION NO. : 12/306332  
DATED : September 15, 2015  
INVENTOR(S) : Megson It is certified that error appears in the above-identified patent and that said Letters Patent is hereby corrected as shown below:

In the Specification:
Column 4, Line 62: Please correct "S-nitroso glutathione."
 to read -- S-nitrosoglutathione. --

Column 5, Line 15: Please correct "(EC$_{8O}$))" to read -- (EC$_{80}$) --

In the Claims:
Column 10, Claim 1, Line 20: Please correct "S-nitrosogiutathione"
 to read -- S-nitrosoglutathione --

Signed and Sealed this
Fifth Day of April, 2016

Michelle K. Lee
*Director of the United States Patent and Trademark Office*